United States Patent [19]

Morgan et al.

[11] Patent Number: 5,237,989
[45] Date of Patent: Aug. 24, 1993

[54] CARDIAC DEFIBRILLATOR WITH MOVABLE CONTACT SWITCH

[75] Inventors: Carlton B. Morgan, Bainbridge Island; Joseph E. Szyperski, Seattle, both of Wash.

[73] Assignee: Physio-Control Corporation, Redmond, Wash.

[21] Appl. No.: 681,347

[22] Filed: Apr. 4, 1991

[51] Int. Cl.⁵ .............................................. A61N 1/39
[52] U.S. Cl. ........................................................ 607/5
[58] Field of Search ........... 128/419 D, 419 B, 419 R, 128/419 P, 419 PS

[56] References Cited

U.S. PATENT DOCUMENTS

| | | | |
|---|---|---|---|
| 3,093,136 | 6/1963 | Lohr | 128/423 |
| 3,211,154 | 10/1965 | Becker et al. | 128/419 D |
| 3,224,447 | 12/1965 | Becker et al. | 128/419 D |
| 3,241,555 | 3/1966 | Caywood et al. | 128/419 D |
| 3,359,984 | 12/1967 | Daniher et al. | 128/419 D |
| 3,389,704 | 6/1968 | Buchowski et al. | 128/419 D |
| 3,865,101 | 2/1975 | Saper et al. | 128/2.06 R |
| 3,913,588 | 10/1975 | Klomp | 128/419 D |
| 4,023,573 | 5/1977 | Pantridge et al. | 128/419 D |
| 4,510,935 | 4/1985 | Spencer | 128/419 D |
| 4,848,345 | 7/1989 | Zenkich | 128/419 D |
| 4,922,906 | 5/1990 | Takeuchi et al. | 128/419 R |
| 5,012,814 | 5/1991 | Mills et al. | 128/419 D |

FOREIGN PATENT DOCUMENTS

| | | | |
|---|---|---|---|
| 0864362 | 4/1961 | United Kingdom | 128/419 D |
| 2032279 | 5/1980 | United Kingdom | 128/419 D |

Primary Examiner—Kyle L. Howell
Assistant Examiner—Kennedy J. Schaetzle
Attorney, Agent, or Firm—Christensen, O'Connor, Johnson & Kindness

[57] ABSTRACT

Disclosed is a cardiac defibrillator for providing a cardiac defibrillation pulse to a patient. The defibrillator comprises a switch contact (14) mounted on a movable switch (10) that moves between a charge position and a discharge position. In the charge position, the switch contact is coupled to a high-voltage battery (22) in order to provide a charge to an energy storage capacitor (30). When the movable switch is released from the charge position, the switch contact engages an electrode contact (32) and a defibrillation pulse flows into a patient (40). The duration of the cardiac defibrillation pulse can be varied by changing the length of time that the switch contact remains engaged with electrode contact. Also disposed within the switch contact path is a discharge contact (42), which is connected to a discharge resistor (48). When the movable switch is in a discharge position, the switch contact is engaged with the discharge contact thereby allowing the discharge resistor to dissipate charge from the energy storage capacitor. A spring (16) is connected to the movable switch in order to rotate it between the charge and discharge positions.

23 Claims, 3 Drawing Sheets 5,237,989

CARDIAC DEFIBRILLATOR WITH MOVABLE CONTACT SWITCH

FIELD OF THE INVENTION

The present invention relates to cardiac defibrillators in general and, in particular, to low-cost, portable cardiac defibrillators.

BACKGROUND OF THE INVENTION

One of the most common and life-threatening heart irregularities is ventricular fibrillation in which the heart is unable to pump a significant volume of blood. When such an irregularity occurs, serious brain damage and death will invariably result unless a normal heart rhythm can be restored within a few minutes. Ventricular fibrillation is often induced as a result of a heart attack but may also be induced by accidental electric shock or due to severe stress such as in the case of surgical operations, drowning, or the like.

The most effective treatment used to restore a normal rhythm to a heart muscle experiencing ventricular fibrillation is the application of a strong electric shock to the victim. Cardiac defibrillators are devices for producing and delivering such shocks and have been known and successfully used for many years. However, the size and cost of prior defibrillators have generally restricted their use to hospitals and emergency medical facilities. Many lives could be saved each year if persons suffering ventricular fibrillation had ready access to a cardiac defibrillator. Therefore, it is an object of the present invention to provide a low-cost, low-maintenance cardiac defibrillator that can be placed in areas in which people are more likely to experience ventricular fibrillation such as near high-voltage electrical equipment.

It is a further object of the invention to provide a cardiac defibrillator having a low-cost, replaceable energy source.

It is a further object of the invention to provide a cardiac defibrillator that can be used in an emergency situation by persons having little medical training.

SUMMARY OF THE INVENTION

The present invention is a cardiac defibrillator capable of delivering a cardiac defibrillation pulse to a patient. The defibrillator includes an electrical energy source and an energy storage means for storing an electrical charge from the electrical energy source. A switch contact moves along a switch contact path from a charge position to a discharge position. An electrode contact is disposed in the switch contact path such that the cardiac defibrillation pulse is delivered to the patient when the switch contact engages the electrode contact. The duration of the cardiac defibrillation pulse is variable by changing the length of the electrode contact that lies in the switch contact path, thereby changing the time that the switch contact and the electrode contact are engaged. In the preferred embodiment, the movable switch contact is mounted on a switch rotor that rotates along an arcuate path between the charge and discharge positions. Means are provided to rotate the switch contact between the charge position and the discharge position.

DETAILED DESCRIPTION OF THE PREFERRED EMBODIMENT

Figure 1:
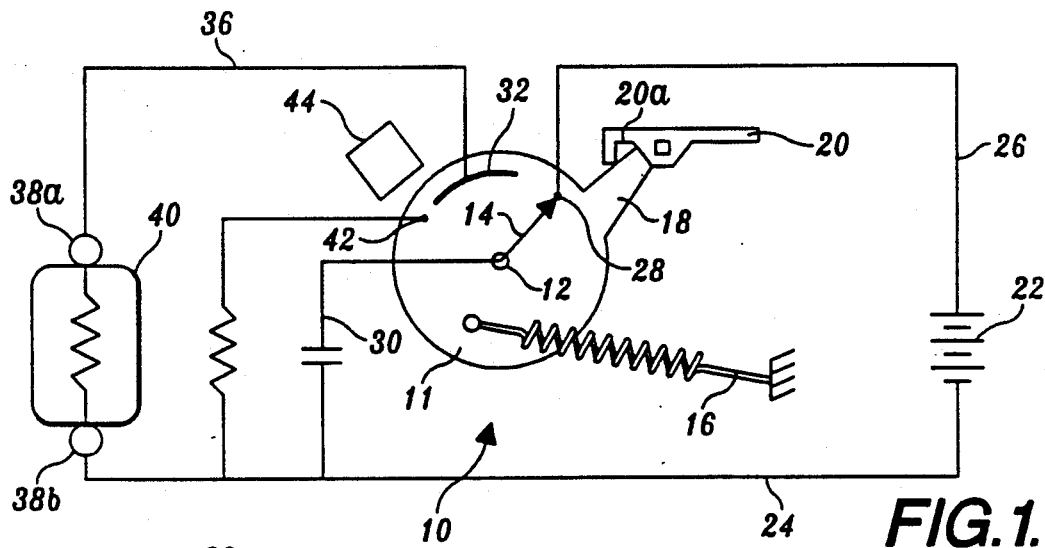
FIG. 1 is an electrical schematic diagram showing a cardiac defibrillator according to the present invention including a switch contact which is shown in a charge position.

FIG. 1 shows an electrical schematic diagram of a cardiac defibrillator according to the present invention. In the preferred embodiment, a movable switch 10 comprises a rotor 11 that pivots about a point 12 under the force of a spring 16. Spring 16 is connected between a chassis (not shown) or some other fixed point of the cardiac defibrillator and a point on the outer circumference of movable switch 10. Upon clockwise rotation of movable switch 10 about pivot point 12, spring 16 is elongated and provides a counterclockwise restoring force. A shock button 20 having a detente portion 20a engages a tang 18, disposed on movable switch 10, to prevent spring 16 from pulling it around pivot point 12.

A high-voltage battery 22 is connected to a common lead 24 and a lead 26 which terminates at a battery contact 28. In order to provide an inexpensive, replaceable energy source, high-voltage battery 22 preferably comprises a stack of lithium calculator or camera-type batteries. Such a stack can easily produce the large electrical potentials needed to charge a capacitor with the necessary energy to produce a cardiac defibrillation pulse of sufficient strength to restore a normal rhythm to a heart muscle experiencing ventricular fibrillation.

An energy storage capacitor 30 is connected between common lead 24 and a switch contact 14 that is disposed on movable switch 10. With movable switch 10 rotated such that tang 18 engages detente 20a, switch contact 14 is electrically connected to battery contact 28, thereby coupling the high-voltage battery 22 to energy storage capacitor 30. Upon releasing tang 18 from detente 20a, movable switch 10 is pulled about pivot point 12 by spring 16 along an arcuate switch path. Disposed within the arcuate switch is an electrode contact 32. As movable switch 10 moves, switch contact 14 engages with electrode contact 32.

Electrode contact 32 is connected by a lead 36 to an electrode 38a that is disposed upon a patient 40. An electrode 38b, also disposed on patient 40 is connected to common lead 24. When switch contact 14 is electrically connected to electrode contact 32, a defibrillation pulse flows from energy storage capacitor 30 through switch contact 14 and electrode contact 32 to electrode 38a. After flowing through patient 40, the defibrillation pulse returns through electrode 38b to common lead 24. The duration of the cardiac defibrillation pulse is determined by the length of time that switch contact 14 remains engaged with electrode contact 32. This duration is governed by the mechanical characteristics of movable switch 10 such as the moment of inertia and the strength (spring constant) of spring 16. The duration of the cardiac defibrillation pulse can be varied by changing the length of electrode contact 32 in order to change the time for which switch contact 14 remains engaged with electrode contact 32. It is also possible to vary the duration of the cardiac defibrillation pulse by increasing or decreasing the strength of spring 16.

Also disposed within the switch path traveled by switch contact 14 is a discharge contact 42. An abutment 44 that is fixed to the chassis (not shown) of the cardiac defibrillator halts the rotation of movable switch 10 about pivot point 12 by halting the rotation of tang 18. When tang 18 rests against abutment 44, switch contact 14 is electrically connected to discharge contact 42. A discharge resistor 48 is connected between common lead 24 and discharge contact 42 so that when switch contact 14 is connected to discharge contact 42, any electric charge still stored in energy storage capacitor 30 is dissipated into discharge resistor 48.

Figure 2:
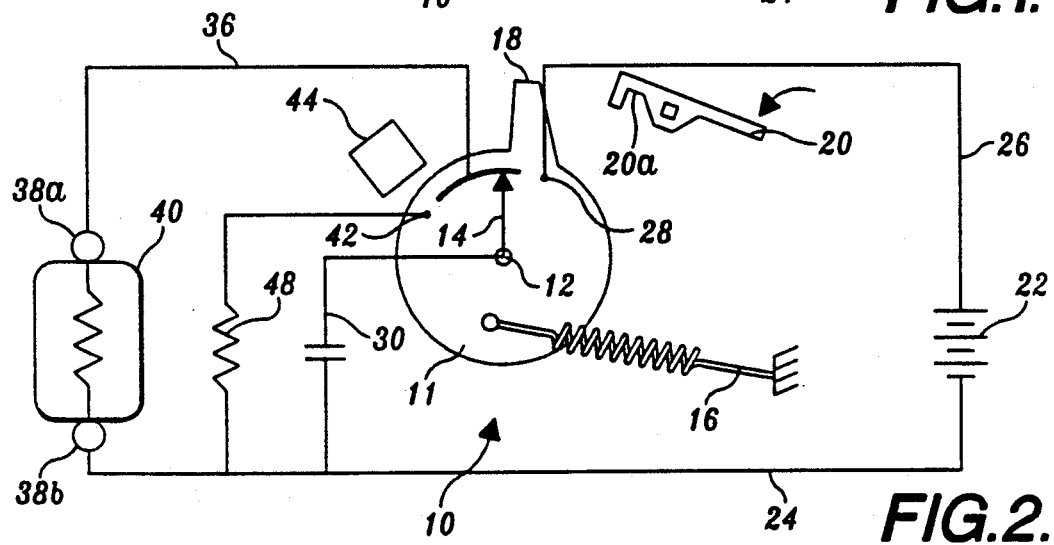
FIG. 2 is an electrical schematic diagram showing the cardiac defibrillator according to the present invention, wherein the switch contact is shown moving from the charge position to a discharge position.

FIG. 2 shows the movement of switch contact 14 after tang 18 has been released from detente 20a. By pressing shock button 20, movable switch 10 is pulled by spring 16 around pivot point 12. Switch contact 14 disengages battery contact 28 and engages electrode contact 32 to deliver a cardiac defibrillation pulse to patient 40.

Figure 3:
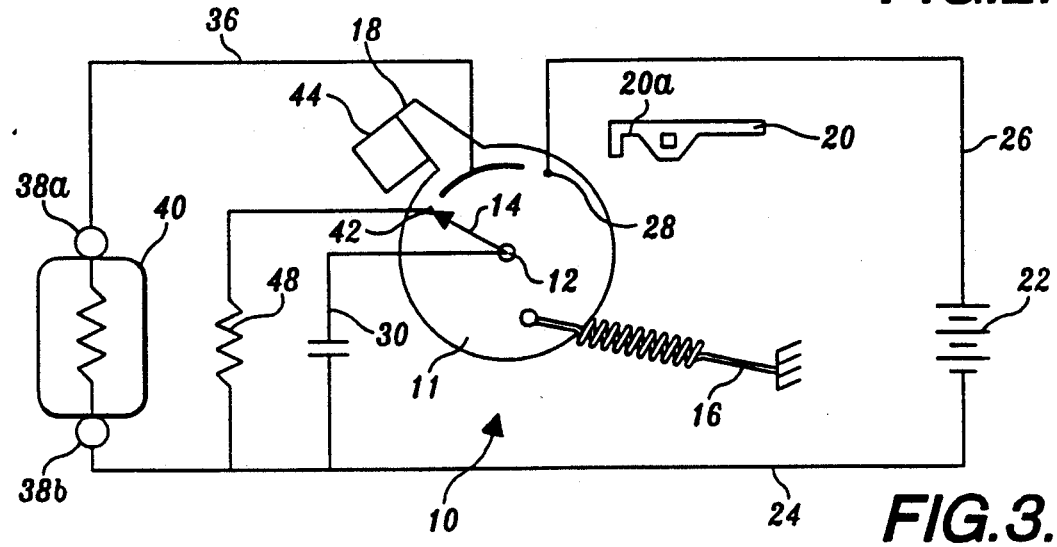
FIG. 3 is an electrical schematic diagram of the cardiac defibrillator according to the present invention, wherein the switch contact is shown in the discharge position.

FIG. 3 shows the cardiac defibrillator according to the present invention in the discharge position. In the discharge position, switch contact 14 is electrically connected to discharge contact 42, thereby allowing discharge resistor 48 to dissipate electric charge that remains on energy storage capacitor 30.

Figure 4:
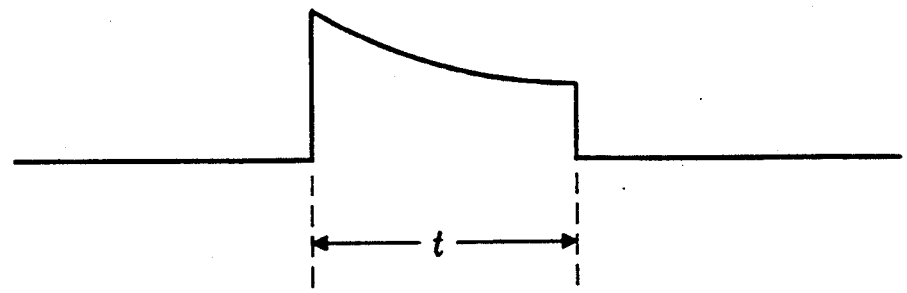
FIG. 4 is a diagram showing a defibrillation pulse produced by a first embodiment of the invention.

FIG. 4 shows a waveform of the cardiac defibrillation pulse that is delivered to patient 40 as switch contact 14 engages electrode contact 32. The duration of the defibrillation pulse, t, is determined by the length of time that switch contact 14 remains engaged with electrode contact 32. The magnitude and rate of decay of the cardiac defibrillation pulse are determined by the electrical characteristics of the circuit, namely, the magnitude of the voltage supplied by high-voltage battery 22, the capacitance of energy storage capacitor 30, and the impedance of patient 40 plus electrodes 38a and 38b. Upon the engagement of switch contact 14 with electrode contact 32, the voltage applied to patient 40 jumps abruptly and decays exponentially. The duration, t, of the defibrillation pulse can be adjusted by increasing or decreasing the length of electrode contact 32 as described above.

Figure 5:
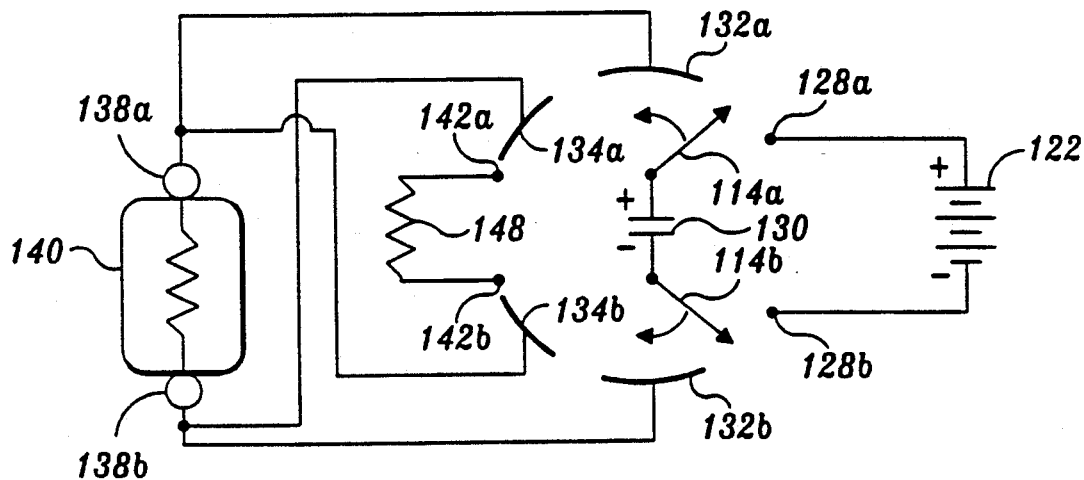
FIG. 5 is a second embodiment of the cardiac defibrillator according to the present invention.

FIG. 5 is a schematic diagram of a second embodiment of the cardiac defibrillator according to the present invention. A switch contact comprises two switch contacts 114a and 114b that are mechanically coupled. Switch contacts 114a and 114b are each connected to the plates of an energy storage capacitor 130. A high-voltage battery 122 is connected to battery contacts 128a and 128b. With switch contacts 114a and 114b moved in a charge position, high-voltage battery 122 is connected to energy storage capacitor 130 in order to provide an electrical charge to energy storage capacitor 130. Switch contacts 114a and 114b are capable of moving in a switch path from the charge position to a discharge position.

Disposed in the switch path is a first set of electrode contacts 132a and 132b. The first set of electrode contacts 132a and 132b are connected to electrodes 138a and 138b, respectively. Electrodes 138a and 138b are disposed upon a patient 140. As switch contacts 114a and 114b engage the set of electrode contacts 132a and 132b, a defibrillation pulse flows from energy storage capacitor 130 to patient 140. The defibrillation pulse flows from electrode 138a through patient 140 to electrode 138b.

Also disposed within the switch path is a second set of electrode contacts 134a and 134b. Electrode contacts 134a and 134b are connected to electrodes 138b and 138a, respectively. When switch contacts 114a and 114b engage the second set of electrodes 134a and 134b, a second defibrillation pulse flows into patient 140. The second defibrillation pulse flows from electrode 138b through patient 140 to electrode 138a. Thus, the second defibrillation pulse has a polarity that is opposite to the first defibrillation pulse. Finally, disposed within the switch path is a set of discharge contacts 142a and 142b. Connected between discharge contacts 142a and 142b is a discharge resistor 148. When switch contacts 114a and 114b engage discharge contacts 142a and 142b, discharge resistor 148 dissipates electric charge stored on energy storage capacitor 130. Preferably, switch contacts 114a and 114b are disposed on a movable switch of the type shown in FIG. 1, although other switch configurations would be apparent to those skilled in the art.

Figure 6:
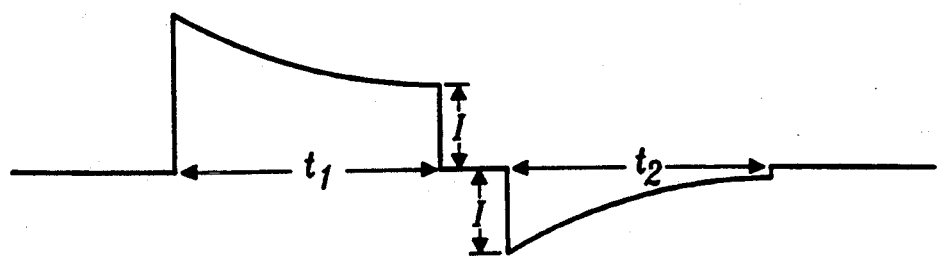
FIG. 6 is a diagram showing a biphasic defibrillation pulse produced by the second embodiment of the invention.

FIG. 6 shows a biphasic cardiac defibrillation wave form of the type produced by the cardiac defibrillation circuit shown in FIG. 5. A first cardiac defibrillation pulse has a duration $t_1$, which is determined by the length of time switch contacts 114a and 114b remain engaged with electrode contacts 132a and 132b, respectively. A second defibrillation pulse has a duration $t_2$, which is determined by the length of time switch contacts 114a and 114b remain engaged with electrode contacts 134a and 134b, respectively. Because the second cardiac defibrillation pulse is obtained by reversing the polarity of the energy storage capacitor 130, the magnitude of the pulse, I, will depend on how much charge remains on energy storage capacitor 130. As with the first embodiment of the cardiac defibrillator described above, the duration of the cardiac pulses $t_1$ and $t_2$ can be varied by increasing or decreasing the length of electrode contacts 132a, 132b, 134a, and 134b to obtain the optimum length for the cardiac defibrillation pulses.

Figure 7:
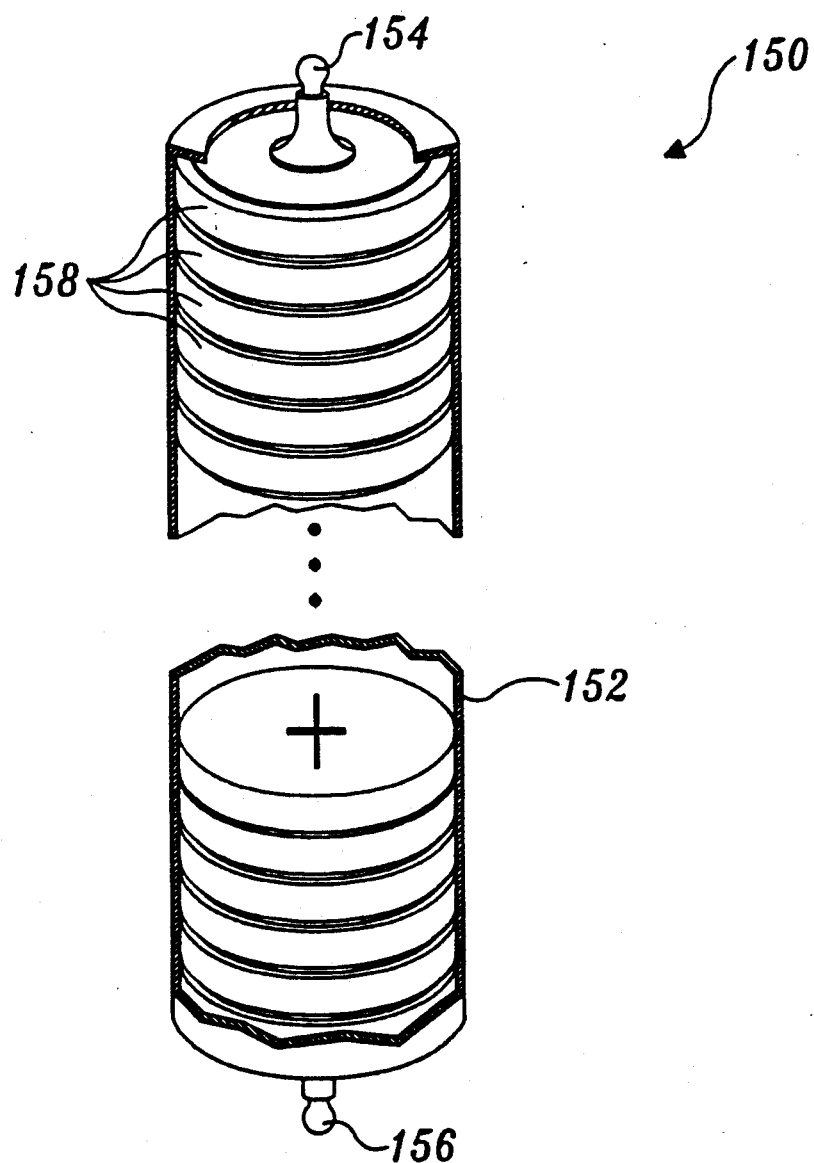
FIG. 7 is a diagram showing a configuration of disc type batteries as used in the present invention.

FIG. 7 shows a high-voltage battery 150 as used in the present invention. High-voltage battery 150 comprises a plurality of disc type batteries 158 of the type commonly found in cameras or calculators. The plurality of batteries is arranged in a stack, such that all the batteries within the stack are in a series relationship. Placed at the top of the stack is a first terminal plate 154, while a second terminal plate 156 is located at the bottom of the stack. The terminal plates 154 and 156 allow electrical leads to be easily connected to high-voltage battery 150. The stack of batteries is held in place by a sleeve 152 that some elastic properties so that the individual batteries remain in contact with one another. In the preferred embodiment, sleeve 152 comprises a length of shrink tubing that pulls the individual batteries 158 as well as the terminal plates 154 and 156 together when heated.

In order to generate the electrical potential needed to produce a cardiac defibrillation pulse of sufficient strength to restore a normal rhythm heart muscle experiencing ventricular fibrillation, voltages of approximately 3,000 volts are needed. Therefore, if each battery 158 within the stack of batteries is rated at three volts, 1,000 batteries are needed to provide a cardiac defibrillation pulse of sufficient strength. Because one stack of 1,000 batteries is cumbersome, it is preferable to connect in series several smaller stacks of batteries to achieve the necessary voltage levels.

The number of batteries needed to produce a defibrillation pulse can be reduced by increasing the capacitance of the energy storage capacitors 30 and 130. However, by increasing the capacitance, the time constant of the defibrillation also increases. If this time constant exceeds approximately 20 milliseconds, the defibrillation pulse may be ineffective in terminating ventricular fibrillation. Therefore, there is an upper limit to how large the capacitance of energy storage capacitors 30 and 130 can be and still be effective in the defibrillator circuit.

Although the present invention has been disclosed with respect to the preferred embodiment, those skilled in the art will realize that changes could be made without departing from the spirit and scope of the invention. For example, movable switch 10 could easily be made to travel in a linear path instead of using a rotor 11. Also, the length of the defibrillation pulse could be varied by increasing the width of switch contact 14 instead of increasing the length of electrode contact 32. Therefore it is intended that the scope of the invention be determined only from the following claims.

The embodiments of the invention in which an exclusive property of privilege is claimed are defined as follows:

1. A cardiac defibrillator for delivering a cardiac defibrillation pulse to a patient comprising:
    an electrical energy source;
    an energy storage capacitor for storing an electrical charge from the electrical energy source;
    a movable switch capable of moving between a charge position and a discharge position;
    a first electrical contact connected to the movable switch such that the first electrical contact moves in a contact path as the movable switch moves between the charge and discharge positions, the first electrical contact being electrically coupled to the energy storage capacitor; and
    a second electrical contact disposed within the contact path and connectable to means for delivering the cardiac defibrillation pulse to the patient, the second electrical contact selected from a plurality of contacts, each having a different contact length, wherein the cardiac defibrillation pulse is delivered to the patient when the first and second electrical contacts are engaged, the duration of the cardiac defibrillation pulse being variable by changing the contact length of the second electrical contact that is disposed in the contact path thereby varying the length of time that the first and second electrical contacts are engaged.

2. A cardiac defibrillator for delivering a cardiac defibrillation pulse to a patient comprising:
    an electrical energy source;
    an energy storage capacitor for storing an electrical charge from the electrical energy source;
    a movable switch capable of moving between a charge position and a discharge position;
    a first electrical contact connected to the movable switch such that the first electrical contact moves in a contact path as the movable switch moves between the charge and discharge positions, the first electrical contact being electrically coupled to the energy storage capacitor;
    a second electrical contact disposed within the contact path and connectable to means for delivering the cardiac defibrillation pulse to the patient, wherein the cardiac defibrillation pulse is delivered to the patient when the first and second electrical contacts are engaged, the duration of the cardiac defibrillation pulse being variable by changing the length of the second electrical contact that is disposed in the contact path thereby varying the length of time that the first and second electrical contacts are engaged; and
    a third electrical contact disposed in the contact path, wherein the third electrical contact is connected to a discharge resistor that removes charge from the energy storage capacitor when the movable switch is in the discharge position.

3. The cardiac defibrillator as in claim 1, further comprising a battery contact disposed within the contact path such that the energy storage capacitor is coupled to the electrical energy source when the movable switch is in the charge position.

4. The cardiac defibrillator as in claim 1, wherein the movable switch comprises a rotor that is movable in a substantially arcuate path between the charge position and the discharge position.

5. The cardiac defibrillator as in claim 1, further comprising:
    means for moving the movable switch between the charge position and the discharge position.

6. The cardiac defibrillator as in claim 1, further comprising:
    means for latching the movable switch in the charge position and means for releasing the movable switch from the charge position.

7. The cardiac defibrillator as in claim 1, wherein the energy source comprises a high-voltage battery.

8. The cardiac defibrillator as in claim 7, wherein the high-voltage battery comprises a plurality of batteries connected in a series relationship.

9. The cardiac defibrillator as in claim 1, wherein the means for delivering the cardiac defibrillation pulse from the cardiac defibrillator to the patient comprises a pair of electrodes attachable to the patient.

10. The cardiac defibrillator as in claim 5, wherein the means for moving the movable switch comprises a spring.

11. A cardiac defibrillator for applying a defibrillation pulse to a patient, comprising:
    a battery;
    an energy storage capacitor for storing a charge from the battery;
    electrodes connectable to the patient for delivering the defibrillation pulse from the cardiac defibrillator to the patient;
    a switch rotor capable of rotating in a substantially arcuate path between a charge position and a discharge position, the switch rotor further comprising a rotor contact that is electrically coupled to the energy storage capacitor, wherein the rotor contact rotates in a rotor contact path as the switch rotor rotates between the charge and discharge positions;

a battery contact disposed within the rotor contact path such that the battery contact is connected to the switch rotor contact thereby connecting the battery to the energy storage capacitor when the switch rotor is in the charge position; and an electrode contact disposed within the rotor contact path and coupled to the electrodes, the electrode contact selected from a plurality of contacts, each having a different contact length, wherein the defibrillation pulse is delivered to the patient when the rotor contact engages the electrode contact, the duration of the defibrillation pulse being variable by changing the length of the electrode contact that lies in the rotor contact path thereby varying the time that the electrode contact and the rotor contact are engaged as the switch rotor rotates between the charge and discharge positions.

12. A cardiac defibrillator for applying a defibrillation pulse to a patient, comprising:

a battery;

an energy storage capacitor for storing a charge from the battery;

electrodes connectable to the patient for delivering the defibrillation pulse from the cardiac defibrillator to the patient;

a switch rotor capable of rotating in a substantially arcuate path between a charge position and a discharge position, the switch rotor further comprising a rotor contact that is electrically coupled to the energy storage capacitor, wherein the rotor contact rotates in a rotor contact path as the switch rotor rotates between the charge and discharge positions;

a battery contact disposed within the rotor contact path such that the battery contact is connected to the switch rotor contact thereby connecting the battery to the energy storage capacitor when the switch rotor is in the charge position;

an electrode contact disposed within the rotor contact path and coupled to the electrodes, wherein the defibrillation pulse is delivered to the patient when the rotor contact engages the electrode contact, the duration of the defibrillation pulse being variable by changing the length of the electrode contact that lies in the rotor contact path thereby varying the time that the electrode contact and the rotor contact are engaged as the switch rotor rotates between the charge and discharge positions; and a discharge contact disposed within the rotor contact path and connected to a discharge resistor, wherein the discharge contact is connected to the rotor contact when the switch rotor is in the discharge position thereby allowing the discharge resistor to dissipate charge from the energy storage capacitor.

13. The cardiac defibrillator as in claim 11, further comprising:

means for moving the switch rotor from the charge position to the discharge position.

14. The cardiac defibrillator as in claim 11, further comprising:

means for latching the switch rotor in the charge position and means for releasing the switch rotor from the charge position.

15. The cardiac defibrillator as in claim 11, wherein the battery comprises a plurality of disc type batteries stacked in a series relationship.

16. Apparatus for delivering a cardiac defibrillation pulse to a patient's heart muscle comprising:

an electrical energy source;

a switch contact;

means for the moving the switch contact along a switch contact path between a charge position and a discharge position;

an electrode contact disposed in the switch contact path, wherein the cardiac defibrillation pulse is delivered to the patient's heart muscle when the switch contact engages the electrode contact, the duration of the cardiac defibrillation pulse being variable by varying the length of time the switch contact and the electrode contact are engaged; and energy storage means for storing an electrical charge from the electrical energy source, wherein the energy storage means is electrically coupled to the switch contact.

17. The apparatus as in claim 16, further comprising:

a battery contact connected to the electrical energy source and disposed in the switch contact path such that the switch contact engages the battery contact when the switch contact is in the charge position.

18. Apparatus for delivering a cardiac defibrillation pulse to a patient's heat muscle comprising:

an electrical energy source;

a switch contact;

means for moving the switch contact along a switch contact path between a charge position and a discharge position;

an electrode contact disposed in the switch contact path, wherein the cardiac defibrillation pulse is delivered to the patient's heart muscle when the switch contact engages the electrode contact, the duration of the cardiac defibrillation pulse being variable by varying the length of time the switch contact and the electrode contact are engaged;

energy storage means for storing an electrical charge from the electrical energy source;

means for dissipating charge from the energy storage means; and a discharge contact connected to the means for dissipating charge from the energy storage means, wherein the discharge contact is disposed in the switch contact path such that charge is dissipated from the energy storage means when the switch contact is in the discharge position.

19. The apparatus as in claim 18, wherein the means for dissipating charge from the energy storage means comprises a resistor.

20. The apparatus as in claim 18, wherein the means for moving the switch contact between the charge position and the discharge position comprises a spring.

21. Apparatus for delivering a biphasic cardiac defibrillation pulse to a patient comprising:

an electrical energy source;

energy storage means for storing an electrical charge from the electrical energy source;

a switch contact capable of moving along a switch contact path;

means for moving the switch contact along the switch contact path;

a first electrode contact connectable to means for delivering the cardiac defibrillation pulse to the patient and disposed in the switch contact path such that a first cardiac defibrillation pulse having a first polarity is delivered to the patient as the switch contact engages the first electrode contact, the duration of the first cardiac defibrillation pulse being variable by changing the length of the first electrode contact that lies in the switch contact path;

a second electrode contact connectable to means for delivering the cardiac defibrillation pulse to the patient and disposed in the switch contact path such that a second cardiac defibrillation pulse having a second polarity is delivered to the patient as the switch contact engages the second electrode contact, the duration of the second cardiac defibrillation pulse being variable by changing the length of the second electrode contact that lies in the switch contact path; and a discharge contact disposed in the switch contact path, wherein the discharge contact is connected to means for dissipating charge from the energy storage means when the switch contact engages the discharge contact.

22. The apparatus as in claim 21, wherein the switch contact moves between a charge position and a discharge position along the switch contact path.

23. The apparatus as in claim 21, further comprising:
a battery contact connected to the electrical energy source and disposed in the switch contact path such that the energy storage means is connected to the electrical energy source when the switch contact is in the charge position.

* * * * *